United States Patent [19]
Boosen

[11] 3,950,412
[45] Apr. 13, 1976

[54] METHOD FOR THE PRODUCTION OF HALOACETOACETIC ACIDS

[75] Inventor: Karl-Josef Boosen, Visp, Valais, Switzerland

[73] Assignee: Lonza Ltd., Gampel, Valais, Switzerland

[22] Filed: Feb. 11, 1974

[21] Appl. No.: 441,425

Related U.S. Application Data

[60] Continuation-in-part of Ser. No. 151,130, June 8, 1971, abandoned, which is a division of Ser. No. 838,646, July 2, 1969, Pat. No. 3,701,803.

[52] U.S. Cl. .......................... 260/539 R; 260/544 Y
[51] Int. Cl.[2] ..................... C07C 51/04; C07C 51/58
[58] Field of Search ..................................... 260/539

[56] References Cited
UNITED STATES PATENTS

| | | | |
|---|---|---|---|
| 2,209,683 | 7/1940 | Boese | 260/586 |
| 3,701,803 | 10/1972 | Boosen | 260/526 R |

OTHER PUBLICATIONS

Roberts et al., "Basic Principles of Organic Chemistry," W. A. Benjamin, Inc. (1964) pp. 530–531.

Primary Examiner—Richard L. Raymond
Attorney, Agent, or Firm—Christen & Sabol

[57] ABSTRACT

Haloacetoacetic acids of the formula $$R_1CH_2-CO-CR_2R_3-COOH$$

wherein $R_1$ represents chlorine or bromine and $R_2$ and $R_3$ each represents hydrogen, chlorine or bromine, are obtained by converting diketene into a chloro or bromo acetoacetic acid halide by means of chlorine or bromine at a temperature of from about −10° to −40°C, and the acetoacetic chloro or bromoacetoacetic acid halide is converted into the corresponding acid by hydrolysis with a stoichiometrically equivalent (or excess) quantity of water.

9 Claims, 1 Drawing Figure

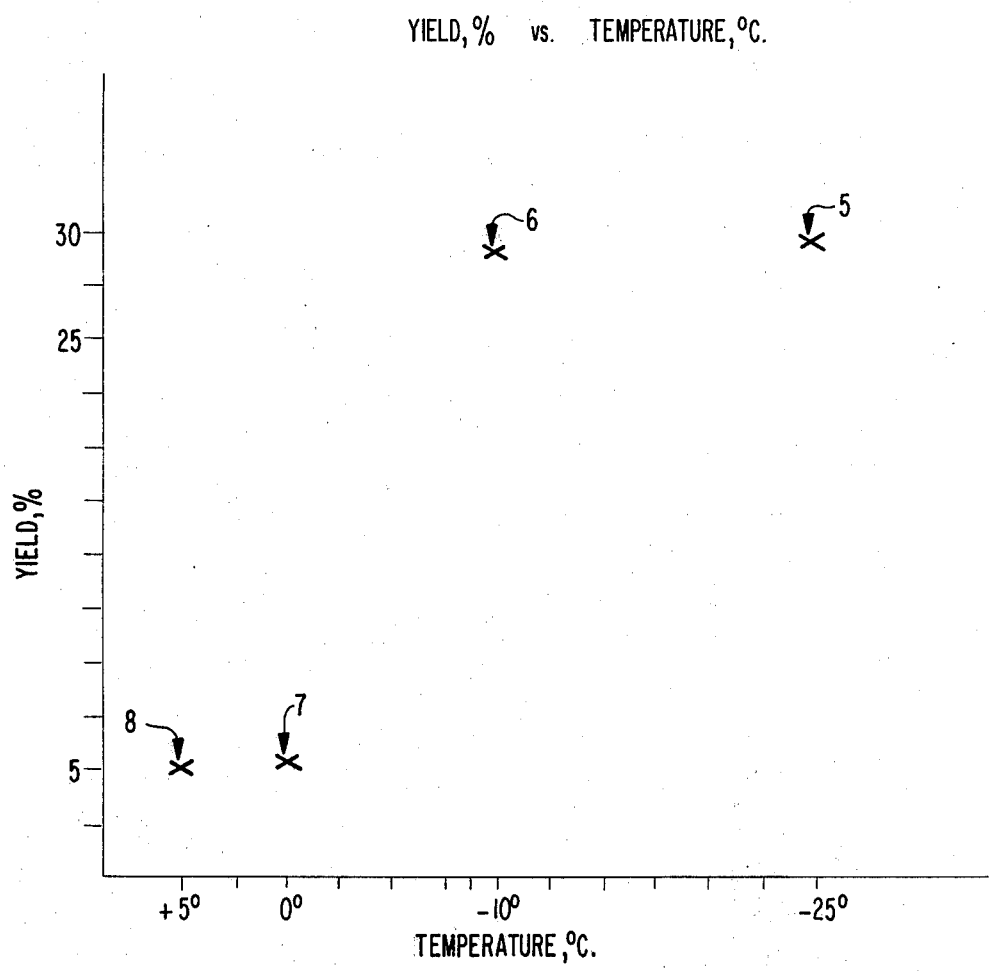

METHOD FOR THE PRODUCTION OF HALOACETOACETIC ACIDS

This application is a continuation-in-part of Patent application Ser. No. 151,130, filed June 8, 1971, now abandoned which in turn is a division of U.S. Patent application Ser. No. 838,646, filed July 2, 1969, now U.S. Pat. No. 3,701,803.

BACKGROUND OF THIS INVENTION

1. Field of this Invention

This invention relates to a process for the production of acetoacetic acids of the general formula $R_1CH_2—CO—CR_2R_3—COOH$, wherein $R_1$ represents bromine or chlorine and $R_2$ and $R_3$ each represents hydrogen, bromine or chlorine.

2. Prior Art

It is known that acetoacetic acid can be prepared by carefully hydrolysing acetoacetic esters with dilute aqueous potassium hydroxide solution at room temperature. In this reaction, the acid formed has to be separated off from any unreacted ester by conversion into its barium salt, and the free acid has to be liberated again from this salt. The free acetoacetic acid obtained in this way is described in the literature as a viscous liquid which cannot be further purified on account of its tendency to decompose into acetone and carbon dioxide.

It is also known that γ-chloro-acetoacetic acid can be prepared by the acid hydrolysis of γ-chloro-acetoacetic ester. The hydrolysis reaction, which is carried out over a period of 45 hours at room temperature with 2 N hydrochloric acid, gives a yield of 46 percent. There is no evidence of the preparation of any other acetoacetic acids in free form.

Attention is directed to U.S. Pat. No. 2,209,683; Roberts et al., "Basic Principles of Organic Chemistry", W. A. Benjamin, Inc., (1964), pp. 530–31; Noller, Carl R., "Chemistry of Organic Compounds," W. B. Saunders Co., (1951), p. 756 Kirk-Othmer, "Encyclopedia of Chemical Technology," 1st Ed., Vol. 1, pp. 143 & 153; Boese, A. B., Ind. Eng. Chem., Vol. 32, (1940), pp. 16–22; and Chick, F., et al., J. Chem. Soc., Vol. 97, (1910), pp. 1980 & 1990.

BROAD DESCRIPTION OF THIS INVENTION

The object of this invention is to prepare highly pure free haloacetoacetic acids in high yields.

According to this invention, the object is achieved in a process for the production of acetoacetic acids having the formula:

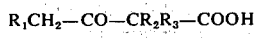

wherein $R_1$ represents bromine or chlorine and $R_2$ and $R_3$ each represents hydrogen, bromine or chlorine, wherein diketene is reacted at a temperature between about $-10°$ C. and about $-40°$ C. with bromine or chlorine to give a acetoacetic acid bromide or chloride, respectively of the formula

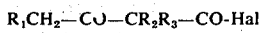

wherein $R_1$, $R_2$ and $R_3$ have the meanings given above and Hal represents bromine or chlorine, and the acetoacetic acid bromide or chloride is hydrolyzed with a stoichiometrically equivalent quantity of water or a quantity of water in excess of the stoichiometrically equivalent quantity at a temperature between about $-10°$ and about $-40°$ C., whereby the desired acetoacetic acid is formed.

γ-haloacetoacetic acid, α,γ-dihaloacetoacetic acid or α,α,γ-trihaloacetoacetic acid is formed, depending upon the quantity of halogen used. Chlorine and bromine are the preferred halogens.

Anhydrous bromide or chloride should be used in the diketene step.

Preferably the diketene reaction steps and the hydrolysis steps are each conducted at a temperature between $-20°$ and $-30°$ C.

The diketene reaction step and the hydrolysis step are each preferably carried out in the presence of a low boiling solvent which is inert both to diketene itself and to halogens.

Examples of such inert solvents are halogenated hydrocarbons, such as, chloroform, dichloroethane, carbon tetrachloride and dichloropropane, and liquid sulphur dioxide. Carbon tetrachloride is preferably used. This has the advantage that the acetoacetic acids are substantially insoluble in cold carbon tetrachloride, so that they can be readily separated off.

The acids are soluble without decomposing in boiling carbon tetrachloride, and crystallize out again substantially quantitatively on cooling.

The halogen derivatives of acetoacetic acid are colorless crystalline substances. The individual acetoacetic acids that can be obtained by the process according to the invention vary in their stability. γ-chloro- and γ-bromoacetoacetic acid are both stable for several weeks when stored at room temperature. The stability of α,γ-dichloroacetoacetic acid and α,α,γ-trichloroacetoacetic acid is similar to that of acetoacetic acid (i.e., stable for several weeks when stored in the dark at temperatures below 0° C. in the absence of air and moisture.) They are also best stored in the dark at temperatures below room temperatures.

DETAILED DESCRIPTION OF THIS INVENTION

This invention is further illustrated by the following non-limiting Examples, and its advantages.

EXAMPLE 1

Acetoacetic Acid 84 gm. of diketene were dissolved in 500 ml of carbon tetrachloride and 37 gm. of gaseous dry hydrogen chloride were introduced into the resulting solution at $-20°$ C. 18 gm. of water were immediately added dropwise to the acetoacetyl chloride formed, which did not have to be isolated, the temperature being kept in the range from $-20°$ to $-30°$ C. The reaction was completed by stirring for 1 hour at $-20°$ to $-30°$ C. The crystals that precipitated were suction-filtered, washed with cold carbon tetrachloride and dried in vacuo at room temperature. Acetoacetic acid, m.p. 31°–33° C., was obtained in a yield of 93.3 gm or 91.5 percent of the theoretical quantity. It was identified by elementary analysis and infra-red spectroanalysis. The ratio of C:H:O was 7.82:1.00:7.95. For comparison, the calculated ratio of C:H:O is 8.00:1.00:8.00.

EXAMPLE 2

γ-chloro-acetoacetic acid 84 gm. of diketene were dissolved in 500 ml of carbon tetrachloride and 71 gm. of chlorine gas were introduced into the resulting solution at −25° C. The γ-chloro-aceto-acetyl chloride formed was immediately hydrolysed, i.e., without being isolated, with 18 gm. of water at −20° to −30° C, and the resulting product was stirred for another hour. The crystallized γ-chloro-acetoacetic acid was suction-filtered, washed with cold carbon tetrachloride and dried at 20° C/20 Torr. γ-chloro-acetoacetic acid, m.p. 66.5°–67.2° C., was obtained in a yield of 104.8 gm. or 76.8 percent of the theoretical quantity. It was identified as described in Example 1.

Calculated: 35.16%, C; 3.66%, H; 35.16%, O; 26.02%, Cl. Found: 35.3%, C; 3.7%, H; 35.1%, O; 26.1%, Cl.

EXAMPLE 3

γ-bromo-acetoacetic acid 84 gm of diketene were dissolved in 500 ml of carbon tetrachloride and 160 gm of bromine dissolved in 200 ml of carbon tetrachloride were added dropwise to the resulting solution at −20° C. Hydrolysis was carried out with 18 gm. of water as described in Example 1. The crystallized γ-bromo-acetoacetic acid was suction-filtered, washed and dried in vacuo. γ-bromoacetoacetic acid, m.p. 69°–69.5° C, was obtained in a yield of 166.8 gm. or 92.1 percent of the theoretical quantity. It was again identified by elementary analysis and infrared spectroanalysis.

Calculated: 26.52%, C; 2.76%, H; 26.52%, O; 44.2%, Br. Found: 26.5%, C; 3.0%, H; 27.2%, O; 44.8% Br.

EXAMPLE 4

α,γ-dichloro-acetoacetic acid

The procedure was as described in Example 2, except that 142 gm. instead of 71 gm. of chlorine were introduced. α,γ-dichloroacetoacetic acid, m.p. 53°–54° C, was obtained in a yield of 133.3 gm. or 78.0 percent of the theoretical quantity. It was again identified by infrared spectroanalysis and elementary analysis.

Calculated: 28.07%, C; 2.34%, H; 28.07%, O; 41.52%, Cl. Found: 27.8%, C; 2.2%, H; 27.7%, O; 40.4%, Cl.

EXAMPLE 5

8.4 gm. of diketene were dissolved in 50 ccm of $CCl_4$, and a stream of dry chlorine was passed through the solution until 7.1 gm. thereof had been absorbed, while maintaining the solution at a temperature of −25° C. The formed γ-chloroacetoacetyl chloride was then hydrolized with 3.9 gm. of water at a temperature of −25° C. Colorless sticky crystals were formed, which were washed with cold $CCl_4$ and then dried at 20° C at 20 torr. The yield was 3.95 gm. or 28.9% of γ-chloroacetoacetyl acid. (From the mother-liquid, 3.7 gm. of monochloroacetone were isolated — this was 40 percent of theoretical.)

EXAMPLE 6

8.4 gm. of diketene were dissolved in 50 ccm of $CCl_4$, and a stream of dry chlorine was passed through the solution until 7.1 gm. thereof had been absorbed, while maintaining the solution at a temperature of −10° C. The formed γ-chloroacetoacetyl chloride was then hydrolyzed with 3.9 gm. of water at a temperature of −10° C. Colorless sticky crystals were formed, which were washed with cold $CCl_4$ and then dried at 20° C. at 20 torr. The yield was 3.85 gm. of 28.1% of γ-chloroacetoacetyl acid. (From the mother-liquid, 3.7 gm. of monochloroacetone were isolated — this was 40 percent of theoretical.)

EXAMPLE 7

As in Example 5, 8.4 gm. of diketene were chlorinated at 0° C. and then, at the same temperature (0° C.), hydrolyzed with water. After filtration, the product was washed with $CCl_4$ and dried. There was obtained 0.72 gm. of γ-chloroacetoacetyl acid which is yield of 5.2% of the theoretical. (From the mother-liquid, 5.65 gm. of mono-chloroacetone was obtained — this was 60 percent of the theoretical.)

EXAMPLE 8

As in Example 5, 8.4 gm. of diketene were chlorinated at +5° C. and then, at the same temperature (+5° C.), hydrolized with water. After filtration, the product was washed with $CCl_4$ and dried. There was obtained 0.70 gm. of γ-chloroacetoacetyl acid which is a yield of 5% of the theoretical. (From the mother-liquid, 5.65 gm. of mono-chloroacetone was obtained — this was 61 percent of the theoretical.)

Example 5 represents this invention, using a preferred temperature of −25° C. during the chlorination and hydrolysis steps. Example 6 represents this invention, using a temperature of −10° C. during the chlorination and hydrolysis steps.

Example 5 (−25° C.) obtained a yield of 28.9 percent of chloroacetoacetyl acid, whereas Example 8 (+5° C.) only obtained a yield of 5 percent of chloroacetoacetyl acid. That is an increase of about 478 percent in yield for the preferred conditions of this invention over the use of a higher reaction temperature. Example 6 obtained a yield of 28.1 percent of chloroacetoacetyl acid, whereas Example 7 only obtained a yield of 5.2 percent. That is an increase of about 440 percent in yield for the conditions of this invention over the use of a higher reaction temperature.

The graph of the Figure is a plot of percent yield vs. reaction temperature for Examples 5 through 8.

(Examples 5 and 6 also show that there is some production, i.e., 40 percent of theoretical, of unwanted monochloroacetone due to decarboxylation during the hydrolysis step even at low temperatures used in this application.)

What is claimed is:

1. A method for the production of acetoacetic acids having the formula:

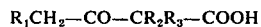

wherein $R_1$ represents bromine or chloride and $R_2$ and $R_3$ each represents hydrogen, bromine or chlorine, wherein diketene is reacted at a temperature between about −10° C. and about −40° C., with bromine or chlorine to give a acetoacetic acid bromide or chlorine, respectively, of the formula

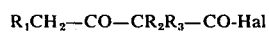

wherein $R_1$, $R_2$ and $R_3$ have the meanings given above and Hal represents bromine or chlorine, and said acetoacetic acid bromide or chloride is hydrolyzed with a stoichiometrically equivalent quantity of water or a quantity of water in excess of the stoichiometrically equivalent quantity at a temperature between about −10° C. and about −40° C., whereby said acetoacetic acid is formed.

2. A method according to claim 1 wherein said diketene is reacted with said bromine or chlorine and said acetoacetic acid bromide or chloride is hydrolyzed with water in the presence of an inert solvent.

3. A method according to claim 2 wherein said insert solvent is carbon tetrachloride.

4. A method according to claim 2 wherein said inert solvent is a halogenated hydrocarbon.

5. A method according to claim 2 wherein $R_2$ and $R_3$ are each hydrogen and wherein the diketene reaction step and the hydrolysis step are each conducted at a temperature between $-20°$ and $30°$ C.

6. A method according to claim 2 wherein anhydrous chlorine or bromine is used in the diketene reaction step.

7. A method according to claim 1 wherein $R_2$ and $R_3$ are each hydrogen and wherein the diketene reaction step and the hydrolysis step are each conducted at a temperature between $-20°$ and $-30°$ C.

8. A method according to claim 2 wherein $R_2$ and $R_3$ are each bromine or chlorine.

9. A method according to claim 2 wherein $R_2$ and $R_3$ are each hydrogen.

* * * * *